United States Patent [19]

Maaskant et al.

[11] Patent Number: 4,623,628

[45] Date of Patent: Nov. 18, 1986

[54] BINDER FOR LOW DENSITY LIPOPROTEINS

[75] Inventors: Nico Maaskant, Hengelo; Adriaan Bantjes, Enschede; Hermanus J. M. Kempen, Leiden, all of Netherlands

[73] Assignee: Organon Teknika b.v., Boxtel, Netherlands

[21] Appl. No.: 748,951

[22] Filed: Jun. 26, 1985

[30] Foreign Application Priority Data

Jun. 27, 1984 [NL] Netherlands ................ 8402021

[51] Int. Cl.$^4$ ........................................... G01N 31/00
[52] U.S. Cl. ..................................... 436/13; 436/16; 436/8
[58] Field of Search ...................... 436/8–19; 424/2; 435/810, 4; 252/408; 422/61; 568/852

[56] References Cited

U.S. PATENT DOCUMENTS

| | | | |
|---|---|---|---|
| 3,955,925 | 5/1976 | Proksch et al. | 436/12 |
| 4,474,887 | 11/1984 | Maier et al. | 436/21 |
| 4,536,274 | 8/1985 | Papadakis et al. | 204/56 R |

FOREIGN PATENT DOCUMENTS

| | | |
|---|---|---|
| 0168093 | 1/1986 | European Pat. Off. . |
| 3133937 | 3/1983 | Fed. Rep. of Germany . |
| 2533704 | 8/1982 | France . |

*Primary Examiner*—Herbert B. Guynn
*Assistant Examiner*—T. J. Wallen
*Attorney, Agent, or Firm*—Stevens, Davis, Miller & Mosher

[57] ABSTRACT

A binder for low density lipoproteins (LDL) consisting of sulphated polyvinyl alcohol which is cross-linked by the chemical or the physical route to a waterinsoluble product. The binder may be in the form of a hydrogel which is applied or not to a carrier or it may be present on the surface of a polyvinyl alcohol fibre which is preferably in the form of tape having a thickness of 0.1 to 2 μm and a width of 0.5 to 6 μm. The fibre shaped binder is prepared by successively cross-linking with an acidified aqueous solution of glutardialdehyde and sulphating with chlorosulphonic acid.

1 Claim, No Drawings

BINDER FOR LOW DENSITY LIPOPROTEINS

The invention relates to a low density lipoproteins (LDL) binder in the form of sulphated polyvinyl alcohol, and to a process for the preparation of such a binder.

A binder of the type indicated above is disclosed in U.S. Pat. No. 3,955,925.

The binder described therein is applied in the preparation of a stable, optically clear serum which is used as reference material for the assay of human blood serum constituents.

The optically clear serum is obtained by removing three out of four types of lipoproteins, viz. chylomicrons, VLDL (pre-$\beta$-lipoproteins) and LDL ($\beta$-lipoproteins).

The removal is effected by mixing the serum with cations of calcium, manganese or magnesium and subsequently adding a polysulphate, such as sulphated polyvinyl alcohol, resulting in precipitation of a lipoprotein polysulphate complex.

A disadvantage to the known binder is that it removes the lipoproteins only in the presence of calcium ions, manganese ions or magnesium ions. A further disadvantage to the well-known binder is that it is less selective in that prior to isolation of the LDL proteins a fraction of very low density lipoproteins (VLDL) is removed. A solution to the problem of selective isolation of LDL proteins is given in German Patent Specification No. 3,133,937. Selective isolation is realized by using the Na or K salt of sulphated polyvinyl alcohol. In the process described in said patent specification dissolved sulphated polyvinyl alcohol (PVAS) is introduced into blood or plasma. This method is not suitable for use in therapeutics in view of the toxicity risk to the large amount of dissolved PVAS to be used then.

If not complexed with LDL, dissolved PVAS will, along with the treated blood or plasma, be returned to the patient.

The present invention provides a binder of the well-known type indicated above which permits selective isolation of low density lipoproteins (LDL) without requiring any further additives.

The invention consists in that with a binder of the well-known type indicated above in the opening paragraph the polymer is cross-linked to a waterinsoluble product. Surprisingly, it has been found that cross-linking the PVAS does not or hardly result in any change of the binding capacity for LDL. Consequently, the LDL binder according to the invention is particularly suitable to be used for clinical removal of LDL proteins from blood or blood serum in an extracorporeal treatment.

By sulphated polyvinyl alcohol is to be understood according to the invention a polymer derived from a polyvinyl alcohol, of which polymer at least 20% of the vinyl alcohol groups are sulphated.

The molecular weight of the polyvinyl alcohol is not critical as long as it can still be cross-linked. This will generally be the case at a molecular weight of 5000 or higher. Very favourable results may be obtained at molecular weights in the range of 10,000 to 150,000 or higher.

According to the invention is it preferred that use should be made of a binder of which at least 50% of the vinyl alcohol groups is sulphated. Optimum results are obtained using binders of which at least 65% of the vinyl alcohol groups is sulphated.

Sulphation of the polyvinyl alcohol is preferably carried out using a reaction product of sulphur trioxide or chlorosulphonic acid and a Lewisbase. Particularly suitable is the addition product of pyridine to sulphur trioxide. The sulphation reaction is preferably carried out in dimethyl formamide or formamide at a temperature between 0° and 60° C.; the reaction time may vary from ½ to 6 hours.

Alternatively, the sulphation reaction may be carried out in excess pyridine in the absence of a solvent. The reaction temperature is chosen then between 60° and 110° C., preferably between 100° and 105° C.

The amount of sulphating agent depends on the degree of substitution desired and can readily be determined experimentally.

The polyvinyl alcohol may be cross-linked before or after sulphation and the cross-linking may be effected by the chemical or the physical route. Chemical cross-linking is carried out preferably using a bifunctional compound of the formula X-R-Y, where X and Y have the meaning of a halogen atom, an aldehyde group or an epoxy group and R is an aliphatic group with 3 to 10 carbon atoms. As examples of suitable cross-linking agents may be mentioned 1,3-dichloro-2-propanol, glutardialdehyde, epichlorohydrin, dichlorohydrin, dibromopropanol, 1,2,3,4-diepoxybutane, bisepoxypropyl ether, ethylene-glycol-bis-epoxy-propyl ether and 1,4-butane diol bisepoxypropyl ether. In case the cross-linking reaction of the polyvinyl alcohol with the cross-linking agent is carried out in the presence of an aqueous base, first of all the use is considered of sodium hydroxide or potassium hydroxide or quaternary ammonium compounds.

Very favourable results have also been obtained when cross-linking is effected physically by $\gamma$-irradiation to form a water-insoluble product. The irradation dose to be used then may vary within wide limits. It is governed by the concentration, the molecular weight of the polymer in solution and the degree of sulphation and the desired degree of cross-linking.

When the degree of cross-linking is too low, the binder will tend to go into solution, particularly when use is made of a polymer of a relatively low molecular weight. Another disadvantage to a low degree of cross-linking is the resulting low strength and dimensional stability. When the degree of cross-linking becomes too high, the LDL binding will very much decrease as a result of a too finely meshed network. This will be the case when the average pore size of the cross-linked polymer decreases to below 20–22 nm (=average diameter of LDL particles).

For a ready diffusion of LDL through the network preference is given to a PVAS with a considerably lower cross-linking density.

A further disadvantage to a high degree of cross-linking is that it may lead to a relatively brittle polymer. For a man skilled in the art it will not be difficult to find such optimum process conditions for each cross-linking agent and appurtenant polymer as will lead to a good binder displaying a high capacity for removing LDL proteins and of which the physical properties are such that it is suitable for clinical use.

After cross-linking the binder will be in the form of a hydrogel, applied or not to a carrier.

It has been found that generally favourable results are obtained when the binder is so cross-linked that after swelling in a physiological salt solution the weight ratio of swollen gel to dry matter is 10 to 75 g/g. Preference is given to a binder which is so cross-linked that after swelling in a physiological salt solution the weight ratio of swollen gel to dry matter is 30 to 50 g/g.

When the LDL binder according to the present invention is present on a carrier, use may be made for it of a fibre, which is a polyvinyl alcohol fibre with a large specific surface area which may be in the form of a dog bone, a Y or be in any other form. Preference is given to a fibre in the form of tape having a thickness in the range of from 0.1 to 2 μm and a width in the range of from 0.5 to 6 μm.

The preparation of an LDL binder according to the invention usually comprises the successive steps of first sulphating the polymer to a degree of sulphation in the range of 0.23 to 0.96, dissolving the sulphated polymer in water to a polymer concentration of 10 to 70 percent by weight, and cross-linking the resulting product by the chemical route or subjecting it to a γ-radiation dose of 0.5 to $25 \times 10^4$ Gy and preferably of 2.5 to $10.0 \times 10^4$ Gy.

In the preparation of an LDL binder from fibres use may advantageously be made of a process in which the polyvinyl alcohol is successively cross-linked and sulphated. When use is made of fibres with a large specific surface area, a higher degree of cross-linking may be applied, which results in a product with improved mechanical properties.

According to the invention preference is given to a process in which the fibre polymer is cross-linked by steeping the fibre in an acidified aqueous solution of glutardialdehyde, followed by washing with water and drying, sulphating with chlorosulphonic acid, washing to remove excess of chlorosulphonic acid, steeping in an aqueous sodium hydroxide solution and finally washing successively with water, a physiological buffer solution and water, followed by drying, if required.

The resulting fibre, after being sterilized, may be introduced into a column through which the blood plasma is passed for the removal of LDL. Per treatment the amount of LDL binder required depends on the specific surface area of the fibres and the degree of cross-linking and sulphation.

The invention will be further described in the following examples, which are of course not to be construed as constituting any limitation on the scope of the present invention.

EXAMPLE I

Preparation of sulphated polyvinyl alcohol

To 200 ml of pyridine there were added dropwise, with stirring, 88 ml of chlorosulphonic acid, the pyridine being cooled in order to prevent the temperature from rising to above 80° C. To the resulting mixture there was added a suspension of 44 g of polyvinyl alcohol (PVA) (molecular weight 14000) in 80 ml of pyridine, after which the reaction mixture was kept at a temperature of 100° to 105° C. over a period of 90 minutes. To the resulting thick, yellowish brown viscous mass there were added, after cooling, 200 ml of water, in which the product dissolved. Subsequently, a concentrated NaOH solution was added, with cooling, until the pH was 9 to 11. Next, the pyridine was removed by vacuum distillation. After filtration the solution was dialysed against demineralized water, followed by purification of the sulphated polyvinyl alcohol by precipitation in ethanol. The yield was 133 g (94% of theory). The degree of sulphation (DS) was 0.96.

In the above manner different polyvinyl alcohols were sulphated, their molecular weight ranging from 14000 to 115000. The degree of sulphation was determined both by elementary analysis and by acid hydrolysis with 0.1N HCl for 8 hours at 90° to 95° C. The H+ ions formed as a result of splitting off of the sulphate groups were determined by titration with alkali. The results obtained with the two methods were in good agreement with each other.

EXAMPLE II

Chemical cross-linking of PVAS with 1,3-dichloro-2-propanol 1000 mg of water, 1560 mg of 1,3-dichloro-2-propanol (DCP) and 960 mg of NaOH were stirred to form a homogeneous suspension. To it was added, with stirring, 1 g of PVAS (DS-0.7; molecular weight (MW)—402,000).

After a reaction time of 8 hours at 50° C. the cross-linked product was thoroughly washed to remove the NaOH and equilibrated with a physiological buffer.

EXAMPLE III

Chemical cross-linking of PVAS was glutardialdehyde (GDA)

To a mixture of 1.33 ml of an aqueous solution of 25% by weight of glutardialdehyde and 0.1 ml of 1NHCl was added 1 g of PVAS (DS-0.7; MW-402000). After reaction for 30 minutes at 20° C. the resulting gel was washed and equilibrated with a physiological buffer.

EXAMPLE IV

Cross-linking PVAS by γ-radiation

Various PVAS samples of the molecular weights (MW) and degrees of substitution (DS) given in the table below were each subjected to a particular radiation dose. The table also mentions the swelling equilibrium values of the cross-linked products in a physiological salt solution.

TABLE I

| Mol. weight* (Daltons) | DS | PVAS conc. (g/g) | Radiation dose (.$10^4$ Gy) | Degree of swelling** (g/g) |
|---|---|---|---|---|
| 420000 | 0.71 | 0.15 | 2.5 | 43 |
| 420000 | 0.71 | 0.15 | 5.0 | 40 |
| 420000 | 0.71 | 0.15 | 7.5 | 32 |
| 296000 | 0.80 | 0.15 | 5.0 | 43 |
| 296000 | 0.80 | 0.20 | 5.0 | 36 |
| 37000 | 0.88 | 0.30 | 5.0 | 50 |
| 37000 | 0.88 | 0.35 | 5.0 | 38 |
| 37000 | 0.88 | 0.40 | 5.0 | 34 |

*determined using light scattering
**swelling equilibrium in physiological salt solution expressed in swollen weight/dry weight.

EXAMPLE V

The materials prepared in the Examples II and III were ground and subsequently sieved to binder particles measuring about 100 μm. Prior to use they were equilibrated in a physiological phosphate buffer.

To determine the LDL binding capacity the binder particles were mixed with LDL-containing serum or plasma. The results of the binding experiments for LDL cholesterol carried out at various plasma/binder ratios are given in the table below.

TABLE II

| volume ratio plasma to binder | cross-linking agent | concentration of total cholesterol before | concentration of total cholesterol after treatm. | % bound cholesterol |
|---|---|---|---|---|
| 20:1 | 1.3-dichloro | 4.50 | 1.55 | 66 |
| 40:1 | 2-propanol | 4.50 | 3.39 | 26 |
| 60:1 | (DCP) | 4.43 | 3.81 | 14 |
| 80:1 | | 4.56 | 4.04 | 12 |
| 20:1 | glutardial- | 4.49 | 2.99 | 32 |
| 40:1 | dehyde (GDA) | 4.58 | 3.88 | 16 |
| 60:1 | | 4.54 | 4.23 | 7 |
| 80:1 | | 4.56 | 4.31 | 5 |

The results in the above table clearly show that the percentages of bound cholesterol increase with decreasing plasma to binder ratios.

EXAMPLE VI

The sixth material listed in Table I of Example IV was tested for lipoprotein binding capacity. To that end the plasma or serum to be treated was mixed with the binder particles and shaken for about 30 minutes (incubation time) at 37° C. The volume ratio of binder to plasma was 1:20 in all cases. Before and after the incubation period the lipoproteins were isolated from the treated plasma by density gradient ultracentrifugation. Of the various lipoproteins the amounts of bound cholesterol and triglycerides (TG) were separately measured as a fraction of the total amounts present.

The results are given in the table below.

TABLE III

| Plasma | | cholesterol before incubation (m mol/l) | cholesterol after incubation (m mol/l) | % bound | triglycerides before incubation (m mol/l) | triglycerides after incubation (m mol/l) | % bound |
|---|---|---|---|---|---|---|---|
| A | VLDL | 1.88 | 1.68 | 11 | 1.95 | 2.11 | NS |
| | IDL | 1.79 | 0.34 | 81 | 0.65 | 0.10 | 85 |
| | LDL | 3.47 | 0.97 | 72 | 0.59 | 0.20 | 66 |
| | HDL$_2$ | 0.11 | 0.06 | NS | 0.06 | 0.04 | NS |
| | HDL$_3$ | 0.35 | 0.33 | NS | 0.14 | 0.13 | NS |
| | Rest | 0.09 | 0.11 | NS | 0.04 | 0.05 | NS |
| | Total | 7.69 | 3.49 | 55 | 3.43 | 2.62 | 23 |
| B | VLDL | 1.13 | 0.29 | 74 | 1.05 | 0.56 | 47 |
| | IDL | — | — | — | — | — | — |
| | LDL | 6.79 | 0.31 | 95 | 0.45 | 0.01 | 98 |
| | HDL$_2$ | 0.07 | 0.09 | NS | 0.01 | 0.01 | NS |
| | HDL$_3$ | 0.51 | 0.50 | NS | 0.02 | 0.05 | NS |
| | Rest | 0.12 | 0.10 | NS | 0.02 | 0.01 | NS |
| | Total | 8.62 | 1.29 | 85 | 1.55 | 0.64 | 59 |
| C | VLDL | 1.91 | 1.96 | NS | 3.41 | 3.63 | NS |
| | IDL | — | — | — | — | — | — |
| | LDL | 2.59 | 0.49 | 81 | 0.51 | 0.30 | 41 |
| | HDL$_2$ | 0.06 | 0.06 | NS | 0.07 | 0.05 | NS |
| | HDL$_3$ | 0.48 | 0.50 | NS | 0.19 | 0.18 | NS |
| | Rest | 0.08 | 0.10 | NS | 0.05 | 0.03 | NS |
| | Total | 5.12 | 3.11 | 39 | 4.23 | 4.19 | NS |
| D | VLDL | 2.55 | 0.62 | 76 | 1.47 | 1.01 | 31 |
| | IDL | — | — | — | — | — | — |
| | LDL | 6.90 | 0.37 | 95 | 0.56 | 0.10 | 82 |
| | HDL$_2$ | 0.22 | 0.22 | NS | 0.05 | 0.05 | NS |
| | HDL$_3$ | 0.58 | 0.59 | NS | 0.14 | 0.17 | NS |
| | Rest | 0.09 | 0.08 | NS | 0.03 | 0.01 | NS |
| | Total | 10.34 | 1.88 | 82 | 2.25 | 1.34 | 40 |
| E | VLDL + IDL | 1.41 | 0.30 | 79 | 0.37 | 0.22 | 41 |
| | LDL | 10.40 | 0.98 | 91 | 0.60 | 0.03 | 95 |
| | HDL$_2$ | 0.50 | 0.47 | NS | 0.04 | 0.05 | NS |
| | HDL$_3$ | 0.76 | 0.80 | NS | 0.06 | 0.07 | NS |
| | Rest | 0.11 | 0.11 | NS | 0.00 | 0.01 | NS |
| | Total | 13.18 | 2.66 | 80 | 1.07 | 0.38 | 64 |

The results with 5 different plasmas in the above table show that:
of LDL 70–95% is bound;
IDL is bound to at least the same extent as LDL;
VLDL is not bound or to a far lesser extent, the binding values for VLDL cholesterol invariably being higher than for VLDL triglyceride, which is indicative of a preferential binding of the cholesterol rich subfraction of VLDL;
HDL$_2$ and HDL$_3$ are bound hardly if at all.

EXAMPLE VII

Chemical cross-linking of PVA fibre and sulphating 1 g of partly cross-linked tape-shaped fibres (0.5 μm thick, 2 μm wide) was brought into a mixture of 20 ml of 0.1N HCl and 6 ml of an aqueous solution containing 25% by weight of glutardialdehyde in which the fibre polymer was cross-linked for two days at room temperature, with gentle stirring. After the material had been thoroughly washed with water and dried it was sulphated for 15 to 120 seconds with a mixture of 30 parts by volume of chlorosulphonic acid and 70 parts by volume of chloroform, which had been brought to a temperature of about −60° C. with liquid nitrogen. After the sulphation time mentioned in the table below the fibre was washed out for about 1 minute with a mixture of 95 parts by volume of chloroform and 5 parts by volume of ethanol in order to remove excess of chlorosulphonic acid, and subsequently brought into an aqueous solution containing 1N NaOH.

To remove any leachables contained in it the resulting fibre was thoroughly washed successively with water, a physiological buffer solution, and water. Subsequently, the fibres were equilibrated for a few hours in a physiological buffer solution.

The results of the invention tests on the fibres thus obtained are given in the table below, which also mentioned the sulphation time, the volume ratio fibre to plasma, the cholesterol concentration after incubation and the percentage bound cholesterol. The citrated plasma contained in all 7.60 mMoles cholesterol per liter. The incubation time was always 30 minutes. All binding values have been corrected for the dilution of the plasma by the water contained in the fibre.

TABLE IV

| Sulphation (sec) | Volume ratio plasma/fibre | cholesterol concentration after incubation (m Moles/l) | % bound cholesterol |
|---|---|---|---|
| 15 | 5:1 | 6.83 | 10 |
| 15 | 10:1 | 7.18 | 6 |
| 15 | 15:1 | 7.33 | 4 |
| 15 | 20:1 | 7.56 | 1 |
| 30 | 5:1 | 2.30 | 70 |
| 30 | 10:1 | 4.99 | 34 |
| 30 | 15:1 | 5.83 | 23 |
| 30 | 20:1 | 6.58 | 13 |
| 60 | 5:1 | 2.68 | 65 |

TABLE IV-continued

| Sulphation (sec) | Volume ratio plasma/fibre | cholesterol concentration after incubation (m Moles/l) | % bound cholesterol |
|---|---|---|---|
| 60 | 10:1 | 4.75 | 38 |
| 60 | 15:1 | 5.39 | 29 |
| 60 | 20:1 | 6.51 | 14 |

The results in the above table clearly show that the best results are obtained with fibres sulphated for 30 to 60 seconds. They also show that during incubation with the cholesterol-containing plasma the percentage bound cholesterol increases with decreasing plasma to fiber ratios.

We claim:

1. A process for the manufacture of a fiber shaped binder for low density lipoproteins (LDL), characterized in that a polyvinyl alcohol fiber is cross-linked by steeping the fiber in an acidified aqueous solution of glutardialdehyde, followed by washing with water and drying, sulphating with chlorosulphonic acid, washing to remove excess chlorosulphonic acid, steeping in an aqueous sodium hydroxide solution, and finally washing successively with water, a physiological buffer solution, and water, followed by drying, if required.

* * * * *